United States Patent [19]

Tuan et al.

[11] Patent Number: 5,281,419
[45] Date of Patent: Jan. 25, 1994

[54] BIODEGRADABLE DRUG DELIVERY SYSTEM FOR THE PREVENTION AND TREATMENT OF OSTEOMYELITIS

[75] Inventors: Rocky S. Tuan, Chester Springs; Sheldon S. Lin, Philadelphia, both of Pa.

[73] Assignee: Thomas Jefferson University, Philadelphia, Pa.

[21] Appl. No.: 952,291

[22] Filed: Sep. 28, 1992

[51] Int. Cl.$^5$ .............................. A61K 35/32
[52] U.S. Cl. .................. 424/426; 424/422; 424/423; 424/425; 623/16
[58] Field of Search .......................... 424/426

[56] References Cited

U.S. PATENT DOCUMENTS

| | | | |
|---|---|---|---|
| 5,004,602 | 4/1991 | Hutchinson | 424/423 |
| 5,073,373 | 12/1991 | O'Leary | 424/423 |
| 5,077,049 | 12/1991 | Dunn et al. | 424/423 |
| 5,110,852 | 5/1992 | Gogolewski | 524/108 |

OTHER PUBLICATIONS

Garvin et al., "Treatment of Canine Osteomyelitis with a Biodegradable Antibiotic Implant," 38th Annual Meeting ORS, Wash. D.C., Feb. 17–20, 1992.
Lin et al., "Evaluation of a biodegradable drug delivery system for chronic osteomyelitis," 38th Annual Meeting, ORS, Wash. D.C., Feb. 17–20, 1992.
Robinson et al., "Preparation and degradation of a biodegradable gentamycin delivery system for the treatment of osteomyelitis," 38th Annual Meeting, ORS, Wash. D.C., Feb. 17–20, 1992.
Tsukayama et al., *Orthopedics* 1988, 11, 1285.
Wei et al., "A bioabsorbable delivery system for antibiotic treatment of osteomyelitis," *J Bone Joint Surg 1991*, 73B, 246–52.
Weston et al., 37th Annual Meeting, ORS, Anaheim, Calif., Mar. 4–7, 1991.

*Primary Examiner*—Thurman K. Page
*Assistant Examiner*—Peter F. Kulkosky
*Attorney, Agent, or Firm*—Woodcock Washburn Kurtz Mackiewicz & Norris

[57] ABSTRACT

An antibiotic impregnated fracture fixation device and antibiotic impregnated drug delivery polymer are provided. In a preferred embodiment, a homogenous mixture of thermally melted poly(lactic) acid and at least one antibiotic and/or antibacterial agent are employed.

14 Claims, No Drawings

BIODEGRADABLE DRUG DELIVERY SYSTEM FOR THE PREVENTION AND TREATMENT OF OSTEOMYELITIS

BACKGROUND OF THE INVENTION

Despite the advent of many new antibiotics, osteomyelitis, in particular, chronic osteomyelitis, continues to represent a medical dilemma. Osteomyelitis is a bone infection caused by pyrogenic microorganisms, most commonly, *Staphylococcus aureus*. Infection may reach the bone directly, for example, through the blood stream or by direct extension from infections in adjacent structures. Very often, infection reaches the bone via compound (open) fracture.

Infection may be introduced to a compound fracture at the time of surgery, but more often, the infection is a result of contamination of the open fracture. It is estimated that 60-70% of open fractures are contaminated with various types of bacterial organisms prior to any surgical or antibiotic therapy. The growth of microorganisms in an open fracture environment is enhanced by the impaired vascularity, avascular bone fragments, and loss of skeletal stability. The majority of bacteria cultured from such wounds are either normal skin flora, for example, *Staphylococcus aureus*, Propionibacterium, or Cornybacterium, or environmental contaminants, for example, Clostridium, Pseudomonas, or Mycobacterium. In addition, nosocomial bacteria may colonize in the wound after hospital admission.

Infection may seriously complicate the healing process. Infections are the primary cause of non-union and bony instability following open fractures. Thus, the clinical objective in the treatment of open fractures is not only to stabilize osseous structures, but also to prevent soft tissue and bony infections.

There is a vast array of treatment options for stabilizing open fractures, including external and internal fixation methods. Although external fixation devices have, in theory, a lower potential for infection, statistically the rate of infection following external fixation ranges from 3.5-30%. This rate is comparable to the incidence of infection using internal fixation techniques and antibiotics. In addition, external fixation procedures are fraught with other potential complications. For example, long periods of external pin fixation often result in pin loosening, pin tract infections, and increased incidence of malunion and non-union.

Alternatively, compound fractures may be fixed internally, for example, with plates or intramedullary rods. Such procedures were initially unpopular despite the excellent skeletal fixation because of the increased infection potential with the introduction of a metallic foreign body into the human body. However, stabilization of the open fracture site is critical for local wound healing and the resolution of a potentially infected wound. The stability provided by internal fixation devices far outweighs the disadvantages of the potentially infected foci. As a result, use of internal fixation devices is increasing.

Empiric utilization of antibiotic therapy has been shown to be extremely important in reducing the incidence of infection. The prognosis of patients undergoing antimicrobial therapy is determined by the bactericidal level of antibiotics at the locale of the infected foci. A persistent problem with treating any localized infection by systemic administration of antibiotics is that the relationship between the assayed serum antibiotic concentration and the level present at the infected foci is inconsistent, especially when the foci is traumatized tissue. Antibiotic concentrations are often subtherapeutic due to impaired vascularity at the fracture site, devitalized bony fragments, and/or associated systemic complications. The situation is compounded by the anaerobic conditions of the infected foci that further decrease the effectiveness of antibiotics. Consequently, high doses of parenteral antibiotics must often be used to achieve adequate local concentrations. The high doses are not only costly, but also increase the incidence of systemic side effects, for example, ototoxicity or nephrotoxicity.

The treatment of osteomyelitis due to compound fracture or other cause, often fails due to the inability to achieve adequate antibiotic levels at the infected foci. As a result, the patient may experience many episodes of recurrence and sepsis.

As can be seen from the foregoing, there is a need for materials and methods which enable clinicians to achieve a therapeutically effective concentration of antibiotic at the infected foci. Local therapy methods include local injection, closed irrigation and suction, implantable antibiotic pumps and antibiotic impregnated beads. Tsukayama et al., *Orthopedics*, 11:1285 (Sept. 1988) disclose an example of a non-degradable implant using polymethylmethacrylate (PMMA) beads containing an antibiotic to achieve local concentrations of particular antibiotics at the site of infection. Three of the antibiotics tested, vancomycin, teicoplanin and ciprofloxacin, were found to be active against staphylococci under anaerobic conditions. However, a significant problem with any non-degradable implant is that once the implant is spent, it must be removed.

Accordingly, an implantable biodegradable delivery system is preferred because there is no need for subsequent procedures to remove the implant system. Further, such systems are able to localize the concentration of antibiotic to the area of infection, for example, the bone, while avoiding problems associated with administering high doses of antibiotic systemically.

A few biodegradable drug delivery systems have recently been suggested for the treatment of chronic osteomyelitis. Lin et al., "Evaluation of a biodegradable drug delivery system for chronic osteomyelitis," 38th Annual Meeting, ORS, Washington D.C., Feb. 17-20, 1992; Robinson et al., "Preparation and degradation of a biodegradable gentamycin delivery system for the treatment of osteomyelitis," 38th Annual Meeting, ORS, Washington D.C., Feb. 17-20, 1992; Garvin, et al., "Treatment of Canine Osteomyelitis with a Biodegradable Antibiotic Implant," 38th Annual Meeting, ORS, Washington D.C., Feb. 17-20, 1992; Wei et al., "A bioabsorbable delivery system for antibiotic treatment of osteomyelitis," *J. Bone Joint Surg.* 73B:246-52 (1991). However, such delivery systems have not been demonstrated to be appropriate for use with antibiotics demonstrated to be effective under anaerobic conditions in bones in pathological states.

For example, Wei et al., disclose that a biodegradable carrier of D,L-lactic acid oligomer having an average molecular weight of 9000 can be combined in its powder form with the antibiotic dideoxykanamycin B to form a small rod (approximately 3 mm in diameter by 10 mm in length) to be implanted into a bone via a burr hole made in the bone for the purpose of implanting the rod therein. *J. Bone Joint Surg.* 73(B):246 (Mar. 1991).

However, testing was not conducted on bones in various pathological states. Further, the efficacy of this system for use with any of the antibiotics shown by Tsukayama et al., to be effective under anaerobic conditions similar to those found in infected bone has not been demonstrated. To the contrary, Weston et. al. (37th Annual Meeting, Orthopaedic Research Soc'y, Mar. 4–7, 1991, Anaheim, CA), disclose that ciprofloxacin, an antibiotic demonstrated to be effective under anaerobic conditions, is incompletely released from an implant using poly(L-lactide) as a carrier. Thus, the references suggest that a poly(1-lactide)-ciprofloxacin implant would not be effective for the treatment of osteomyelitis.

There is a heretofore unmet need for biodegradable drug delivery systems that are appropriate for use with compromised bone, for example, fractured bone. Such delivery systems preferably combine an antibiotic efficient under anaerobic conditions, for example an aminoglycoside antibiotic or quinolone, especially ciprofloxacin, with a biodegradable carrier to form an intramedullary rod for use in the reduction of open fractures as well as the prevention and/or treatment of infection.

SUMMARY OF THE INVENTION

Provided herein are novel biodegradable drug delivery systems that are appropriate for use with compromised bone, for example, open or closed fracture bones. The drug delivery systems may comprise antibiotic impregnated fracture fixation devices that combine an antibiotic effective under anaerobic conditions, for example an aminoglycoside antibiotic or quinolone, especially ciprofloxacin, with a biodegradable carrier. The drug delivery systems may also comprise a coating of antibiotic biodegradable drug delivery polymer that may be applied to a fracture fixation system. One particular advantage of the biodegradable drug delivery systems of this invention is that they may be used for the reduction of compound fractures as well as for the prevention and/or treatment of infection.

Also provided herein are methods for forming the biodegradable drug delivery systems of this invention and methods for using the same.

DETAILED DESCRIPTION OF THE INVENTION

Biodegradable drug delivery systems of this invention may comprise antibiotic impregnated fracture fixation devices or may comprise antibiotic impregnated drug delivery polymers. Antibiotic impregnated fracture fixation devices of this invention comprise biodegradable drug delivery devices for use in internal fixation procedures. The fracture fixation devices are a combination of a biodegradable carrier, for example, poly(lactic) acid (PLA), and at least one antibiotic which is effective under anaerobic conditions, for example an aminoglycoside antibiotic or quinolone, especially ciprofloxacin. The fracture fixation devices may take various forms including, for example, rod, pin or plate forms, and may be used for the reduction of compound fractures, as well as to prevent or treat infection. The fracture fixation devices may be inserted intraosseously by techniques known in the art.

In a preferred embodiment, the fracture fixation devices comprise 5 to 30% (w/w) antibiotic and either 2, 50 or 100 kDa PLA. Such devices may be generated by combining the antibiotic with thermally melted PLA (250° C.) to yield a homogenous mixture. The amount of antibiotic and/or molecular weight of PLA may be varied to provide devices that will release antibiotic for varying lengths of time. Suitable antibiotics include aminoglycoside antibiotics and quinolones. In a particularly preferred embodiment the antibiotic is ciprofloxacin. The homogenous mixture of antibiotic and thermally melted PLA is pressure injected into molds and allowed to cool to 20° C. Prior to cooling, the melted composite may be inserted with a support, for example, a metallic plate, rod or pin to enhance mechanical strength. In such instances, the homogenous mixture of antibiotic and thermally melted PLA forms a concentric layer of biodegradable drug delivery system around the support.

The length and diameter of such fracture fixation devices may be varied according to need. The size and shape is varied and determined by the type of bone fractured. The size of the mold is varied to achieve devices of various length and diameter and various configurations, including pin, plate and rod configurations. The mold may comprise various materials, for example, stainless steel or aluminum cast. In a preferred embodiment, the mold comprises Teflon.

The duration of antibiotic release necessary for the treatment of various medical conditions may be varied by using different molecular weights of the polymer and/or varying the amount of antibiotic (w/w). For example, the length of antibiotic therapy for open fracture varies between one and two weeks. In a preferred embodiment for the treatment of an open fracture, a fraction fixation device comprising about 10% w/w Ciprofloxacin and 2 Kda PLA provides an antibiotic release rate that would be appropriate for the duration of time necessary to treat an open fracture.

For the treatment of chronic osteomyelitis, many physicians recommend four to six weeks of parenteral antibiotic therapy. In a preferred embodiment for the treatment of chronic osteomyelitis, a fraction fixation device comprising about 30% w/w Ciprofloxacin and 50 kDa PLA provides sustained antibiotic release for the recommended length of time.

The drug delivery systems may also comprise a composite comprising antibiotic impregnated drug delivery polymer that may be applied to or coated on a fracture fixation system. Antibiotic impregnated polymers are a combination of a biodegradable carrier, for example, PLA, and at least one antibiotic. The size of the fracture fixation system is determined by the size of the fractured bone, which size may vary in accordance with the size and age of the patient. The form of the fracture fixation system may also be varied in accordance with need.

In a preferred embodiment the antibiotic impregnated drug delivery polymer comprises a composite wherein the % antibiotic on a w/w basis may range from between about 5 to 30%, with the optimal percentage about 30%. The molecular size of Poly(lactic) acid (PLA) may range from between about 2 to 100 kDa., with the preferred size of about 50 kDa. The composite may be formed by combining the antibiotic, preferably ciprofloxacin, with thermally melted PLA to yield homogenous mixture to be applied to the fracture fixation system for insertion at the infected foci.

For example, in an open tibia fracture, an intramedullary rod comprising a rod with a concentric layer of the composite coated thereon may be inserted intraosseously by techniques known in the art. In an open forearm fracture, a layer of the composite may be coated on a fracture fixation plate and placed subperiosteally by fracture fixation techniques known in the art.

Further variations and modifications of the aforementioned can, of course, be made without departing from the spirit and scope of the invention as disclosed herein, and those skilled in the art will recognize multiple utilizations of the present invention that are within the scope of this disclosure.

EXAMPLES

Example 1

The efficacy of the PLA-ciprofloxacin composite in vivo was evaluated as follows. Chronic osteomyelitis was induced in the tibia of 18 New Zealand white rabbits using $1.0 \times 10^6$ cfu of S. aureus. After 21 days, the infected foci were treated surgically with debridement and irrigation. After debridement and irrigation, the experimental group (n=12) was implanted with PLA-ciprofloxacin composite (400 mg) while the control group (n=6) was implanted with PLA (without ciprofloxacin) of similar weight. Bone samples were obtained and bacteria concentrations were determined.

One control animal did not develop an established chronic osteomyelitis and one experimental animal died of unrelated causes; upon autopsy, the operated tibia demonstrated healing with no abscesses. Qualitative assessment, bacteria quantification, and roentgenographic examination were performed. Qualitative grading demonstrated a difference between the two respective groups. None of the rabbits in the experimental group contained an abscess with sinus formation while 4 of 5 controls did. Eight of the 11 animals in the experimental group revealed sterile cultures, 2 demonstrated negligible bacteria counts ( 5 cfu/mg and 6 cfu/mg). One experimental animal showed a 93% reduction (from $3.64 \times 10^5$ prior to treatment to $2.63 \times 10^5$ cfu/mg) in bacteria count. This compares favorably to the control group in which 3 animals showed a 3-11 fold increase in bacteria concentration and 1 animal had a count similar to that prior to treatment. None of the 5 controls demonstrated sterility of the infected foci. Results from roentgenographic analysis were similar to the clinical and bacteriologic results. Ciprofloxacin was determined in the tibia of 4 of the 11 animals in the experimental group (mean concentration 9.2 $\mu$g/ml). Successful growth of bacteria on sterile serial dilution plates was used as a positive control.

Example 2

In vivo experiments were conducted in 28 New Zealand white rabbits (2-2.5 kg). PLA-ciprofloxacin implants were inserted intraosseously in the proximal tibia. Levels of ciprofloxacin in cortical bone, cancellous bone, and bone marrow specimens were quantitated over distance from the implant from 4 days to 8 weeks. Serum, muscle, liver and urine concentrations of ciprofloxacin were also obtained concurrently.

The results show that local ciprofloxacin concentrations were greater than the minimal inhibitory concentration (MIC) forty millimeters beyond the implant site up to eight weeks. Bone marrow ciprofloxacin concentration demonstrated a decreasing gradient over distance as well as time. Cortical levels of ciprofloxacin showed similar results, but demonstrated slightly lower concentrations over the same distance and time. Systemic tissue (serum, muscle and liver) ciprofloxacin levels were undetectable in all specimens.

Example 3

In vitro experiments were conducted to determine the optimal percentage of ciprofloxacin and the optimal molecular weight of PLA. Composites of 5, 10 and 30% ciprofloxacin and 2, 50 and 100 kDa. PLA were generated by combining ciprofloxacin with thermally melted PLA to yield homogeneous 150 mg implants. The implants were incubated in 10 ml 0.9% NaCl at 37° C. for approximately 5 weeks, drawing 1 ml aliquots at intervals to determine in vitro release kinetics. Aliquots were stored at 0° C. and a microbiologic disc diffusion assay was performed to quantitate release. Sample and standards were added to a 6 mm disc and placed on LB Agar containing a lawn of S. Aureus. The diameter of the zone of inhibition was measured. The breakpoint sensitivity limit of ciprofloxacin was less than 1.0 $\mu$g/ml.

The in vitro assay demonstrated an initial burst followed by sustained release of ciprofloxacin over 30 days. The release rate decreased with the increasing molecular weight of PLA and increased with the percent incorporation of ciprofloxacin. The release of ciprofloxacin over 30 days ranged from 5% (10%; 100 kDa.), 10% (10%; 50 kDa.), and 70.4% (10%, 2 kDa.). The PLA-ciprofloxacin composite of 30% ciprofloxacin and 50 kDa. PLA demonstrated an average release of 20% by day 14 and 50% by day 30. This composite combination was used for in vivo analysis.

What is claimed:

1. A device for treating a fractured bone, comprising a fracture fixation device comprising a pre-formed composite consisting essentially of a homogenous mixture of thermally melted poly(lactic) acid and at least one antibiotic and/or antibacterial agent selected quinoline antibiotics.

2. The fracture fixation device of claim 1 wherein said antibiotic and/or antibacterial agent comprises ciprofloxacin.

3. The fracture fixation device of claim 2 wherein said poly(lactic)acid has an average molecular size ranging from between about 2 to 100 kDa and ciprofloxacin comprises about 5 to 30% (w/w) of said device.

4. The fracture fixation device of claim 3 wherein said poly(lactic) acid has an average molecular size of about 2 kDa and iprofloxacin comprises about 10% (w/w) of said device.

5. The fracture fixation device of claim 3 wherein said poly(lactic) acid has an average molecular size of about 50 kDa and ciprofloxacin comprises about 30% (w/w) of said device.

6. The fracture fixation device of claim 2 further comprising a plate, rod, or pin upon which said composite of thermally melted poly(lactic) acid and ciprofloxacin is concentrically layered.

7. The fracture fixation device of claim 6 wherein the plate, rod, or pin is metallic.

8. The fracture fixation device of claim 1 wherein the composite is in the form of a rod.

9. The fracture fixation device of claim 1 wherein the homogenous mixture is in the form of a plate.

10. The fracture fixation device of claim 1 wherein the homogenous mixture is in the form of a pin.

11. A device for treating a fractured bone, comprising a fracture fixation device consisting essentially of a homogenous mixture of thermally melted poly(lactic) acid having an average molecular size of from 50-100 kDA and ciprofloxacin selected from the group consisting of quinoline and aminoglycoside antibiotics.

12. The fracture fixation device of claim 11 wherein the device is in the form of a rod.

13. The fracture fixation device of claim 11 wherein the device is in the form of a plate.

14. The fracture fixation device of claim 11 wherein the device is in the form of a pin.

* * * * *

UNITED STATES PATENT AND TRADEMARK OFFICE
CERTIFICATE OF CORRECTION

PATENT NO. : 5,281,419
DATED : 1/25/94
INVENTOR(S) : Tuan et al.

It is certified that error appears in the above-identified patent and that said Letters Patent is hereby corrected as shown below:

Column 4, line 13, delete "delivery" and insert --deliver--.

Column 5, line 37, delete "$3.64 \times 10^5$" and insert --$3.64 \times 10^6$--.

Column 6, line 47, delete "iprofloxacin" and insert --ciprofloxacin--.

Signed and Sealed this

Ninth Day of May, 1995

Attest:

BRUCE LEHMAN

Attesting Officer

Commissioner of Patents and Trademarks